United States Patent
Karch et al.

(10) Patent No.: US 10,123,756 B2
(45) Date of Patent: Nov. 13, 2018

(54) SINGLE SOURCE DUAL ENERGY HAVING TWO FILTERS FOR X-RAY SPECTRUM DIFFERENTIATION IN THE CASE OF RADIATOR SCREENS HAVING SLOTTED PLATES

(71) Applicant: Siemens Healthcare GmbH, Erlangen (DE)

(72) Inventors: Thomas Karch, Bamberg (DE); Alexander Nagel, Egloffstein (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 80 days.

(21) Appl. No.: 15/114,454

(22) PCT Filed: Jan. 30, 2015

(86) PCT No.: PCT/EP2015/051962
§ 371 (c)(1),
(2) Date: Jul. 27, 2016

(87) PCT Pub. No.: WO2015/117899
PCT Pub. Date: Aug. 13, 2015

(65) Prior Publication Data
US 2016/0343462 A1 Nov. 24, 2016

(30) Foreign Application Priority Data
Feb. 10, 2014 (DE) .................. 10 2014 202 330

(51) Int. Cl.
*A61B 6/00* (2006.01)
*A61B 6/03* (2006.01)
(Continued)

(52) U.S. Cl.
CPC ............ *A61B 6/4035* (2013.01); *A61B 6/032* (2013.01); *A61B 6/06* (2013.01); *A61B 6/40* (2013.01);
(Continued)

(58) Field of Classification Search
CPC .. A61B 6/032; A61B 6/06; A61B 6/40; A61B 6/4035; A61B 6/4042; A61B 6/482
(Continued)

(56) References Cited

U.S. PATENT DOCUMENTS

| 4,277,685 A | 7/1981 | Covic et al. |
| 4,731,807 A * | 3/1988 | Plessis ................... A61B 6/032 378/146 |

(Continued)

FOREIGN PATENT DOCUMENTS

| CN | 1885447 A | 10/2005 |
| CN | 101206931 A | 6/2008 |

(Continued)

OTHER PUBLICATIONS

German Decision to Grant and English translation thereof dated Feb. 12, 2015.
(Continued)

*Primary Examiner* — Allen C. Ho
(74) *Attorney, Agent, or Firm* — Harness, Dickey & Pierce, P.L.C.

(57) ABSTRACT

A slotted plate is for limiting an incident x-ray radiation. The slotted plate includes at least one slotted opening and two different x-ray filter regions for x-ray spectrum differentiation of the incident x-ray radiation. The two different x-ray filter regions are permanently arranged in the region of the at least one slotted opening such that radiation portions of the x-ray radiation penetrating the slotted opening having different x-ray spectra can be generated simultaneously. A
(Continued)

radiator screen, an x-ray radiator for generating a radiation beam fan, a computer tomography device having such an x-ray radiator, and a method for controlling such a computer tomography device are also disclosed.

37 Claims, 7 Drawing Sheets

(51) Int. Cl.
  *G21K 1/10* (2006.01)
  *A61B 6/06* (2006.01)
(52) U.S. Cl.
  CPC .......... *A61B 6/4042* (2013.01); *A61B 6/4078* (2013.01); *A61B 6/482* (2013.01); *G21K 1/10* (2013.01)
(58) Field of Classification Search
  USPC .......... 378/5, 16, 98.9, 98.11, 147, 149–151, 378/156–159
  See application file for complete search history.

(56) References Cited

U.S. PATENT DOCUMENTS

| | | | | |
|---|---|---|---|---|
| 4,821,306 A * | 4/1989 | Mulder | A61B 6/06 | 378/146 |
| 6,148,062 A * | 11/2000 | Romeas | G21K 1/04 | 378/156 |
| 6,301,334 B1 * | 10/2001 | Tybinkowski | A61B 6/06 | 378/147 |
| 6,396,902 B2 * | 5/2002 | Tybinkowski | G21K 1/025 | 378/148 |
| 6,501,828 B1 * | 12/2002 | Popescu | A61B 6/06 | 378/145 |
| 6,633,627 B2 * | 10/2003 | Horiuchi | A61B 6/032 | 378/156 |
| 6,711,236 B2 * | 3/2004 | Izuhara | A61B 6/035 | 250/505.1 |
| 6,735,273 B2 * | 5/2004 | Flohr | A61B 6/032 | 378/158 |
| 6,778,636 B1 * | 8/2004 | Andrews | G21K 1/04 | 378/147 |
| 6,862,340 B2 * | 3/2005 | Wurzer | G21K 1/10 | 250/505.1 |
| 6,934,363 B2 * | 8/2005 | Seufert | G21K 1/04 | 378/147 |
| 6,950,493 B2 * | 9/2005 | Besson | A61B 6/032 | 378/16 |
| 6,999,551 B2 * | 2/2006 | Bressel | A61B 6/032 | 378/151 |
| 7,170,975 B2 * | 1/2007 | Distler | A61B 6/032 | 378/147 |
| 7,200,204 B2 * | 4/2007 | Distler | A61B 6/035 | 378/119 |
| 7,254,215 B2 * | 8/2007 | Ross | G21K 1/04 | 378/147 |
| 7,254,216 B2 * | 8/2007 | Thandiackal | A61B 6/032 | 378/157 |
| 7,263,171 B2 * | 8/2007 | Zhang | G21K 1/04 | 250/505.1 |
| 7,284,905 B2 * | 10/2007 | Kühn | A61B 6/032 | 378/119 |
| 7,317,786 B2 * | 1/2008 | Distler | A61B 6/06 | 378/145 |
| 7,330,535 B2 * | 2/2008 | Arenson | G21K 1/04 | 378/157 |
| 7,336,768 B2 * | 2/2008 | Ogawa | A61B 6/06 | 378/156 |
| 7,397,904 B2 * | 7/2008 | Virshup | G21K 1/10 | 378/156 |
| 7,430,282 B2 * | 9/2008 | Mori | A61B 6/032 | 378/145 |
| 7,463,715 B2 * | 12/2008 | Spahn | A61B 6/4035 | 378/114 |
| 7,535,987 B2 * | 5/2009 | Matsuda | G01N 23/046 | 378/159 |
| 7,653,179 B2 * | 1/2010 | Ramsauer | A61B 6/06 | 378/157 |
| 7,680,249 B2 * | 3/2010 | Yuan | A61B 6/00 | 378/156 |
| 7,852,990 B2 * | 12/2010 | Aulbach | G21K 1/04 | 378/148 |
| 8,064,568 B2 * | 11/2011 | Von Der Haar | A61B 6/032 | 378/147 |
| 8,077,830 B2 * | 12/2011 | Brown | A61N 5/1048 | 378/156 |
| 8,130,901 B2 * | 3/2012 | Müller | A61B 6/06 | 378/147 |
| 8,184,776 B2 * | 5/2012 | Yuan | G21K 1/10 | 378/156 |
| 8,199,884 B2 * | 6/2012 | Junjie | G21K 1/04 | 378/150 |
| 8,218,728 B2 * | 7/2012 | Karch | A61B 6/032 | 378/156 |
| 8,238,522 B2 * | 8/2012 | Frey | A61B 6/06 | 378/156 |
| 8,265,228 B2 * | 9/2012 | Shaw | G21K 1/025 | 378/154 |
| 8,284,903 B2 * | 10/2012 | Yuan | A61B 6/06 | 378/156 |
| 8,311,182 B2 * | 11/2012 | Chandra | A61B 6/03 | 378/5 |
| 8,331,536 B2 * | 12/2012 | Shaw | A61B 6/06 | 378/154 |
| 8,553,835 B2 * | 10/2013 | Hangartner | A61B 6/032 | 378/157 |
| 8,571,178 B2 * | 10/2013 | Sendai | A61B 6/4042 | 378/157 |
| 8,798,230 B2 * | 8/2014 | Cho | A61B 6/03 | 378/15 |
| 8,853,636 B2 * | 10/2014 | Perkins | A61N 5/1042 | 250/363.1 |
| 8,926,177 B2 * | 1/2015 | Ikhlef | A61B 6/032 | 378/207 |
| 8,995,619 B2 * | 3/2015 | Gray | G01V 5/0025 | 378/57 |
| 9,008,264 B2 * | 4/2015 | Boone | A61B 6/583 | 378/207 |
| 9,014,339 B2 * | 4/2015 | Grodzins | G01N 23/046 | 359/233 |
| 9,014,341 B2 * | 4/2015 | Zhang | A61B 6/03 | 250/394 |
| 9,020,103 B2 * | 4/2015 | Grodzins | G21K 1/046 | 359/223.1 |
| 9,050,059 B2 * | 6/2015 | Kuwabara | A61B 6/542 | |
| 9,052,271 B2 * | 6/2015 | Grodzins | G01N 23/203 | |
| 9,125,613 B2 * | 9/2015 | Gregerson | A61B 6/4488 | |
| 9,159,462 B2 * | 10/2015 | Rossi | A61B 6/032 | |
| 9,183,961 B2 * | 11/2015 | Fadler | G21K 1/10 | |
| 9,204,852 B2 * | 12/2015 | Edic | A61B 6/482 | |
| 9,208,918 B2 * | 12/2015 | Tybinkowski | G21K 1/02 | |
| 9,218,933 B2 * | 12/2015 | Langeveld | H01J 37/1472 | |
| 9,230,701 B2 * | 1/2016 | Teng | G21K 1/02 | |
| 9,254,109 B2 * | 2/2016 | Becker | A61B 6/032 | |
| 9,295,437 B2 * | 3/2016 | Saito | G21K 1/046 | |
| 9,312,038 B2 * | 4/2016 | Takagaki | A61B 6/06 | |
| 9,390,825 B2 * | 7/2016 | Lee | G21K 1/10 | |
| 9,424,958 B2 * | 8/2016 | Vogtmeier | G21K 1/10 | |
| 9,480,443 B2 * | 11/2016 | Feuerlein | A61B 6/032 | |
| 9,504,439 B2 * | 11/2016 | Yi | A61B 6/5205 | |
| 9,689,815 B2 * | 6/2017 | Jones | G01N 23/223 | |
| 9,743,901 B2 * | 8/2017 | Yi | A61B 6/4035 | |
| 9,763,632 B2 * | 9/2017 | Notohara | A61B 6/4035 | |
| 9,791,384 B2 * | 10/2017 | Sung | G01N 23/04 | |
| 9,820,709 B2 * | 11/2017 | Melman | G21K 1/04 | |
| 9,820,715 B2 * | 11/2017 | Kang | A61B 6/542 | |
| 9,848,840 B2 * | 12/2017 | Ohashi | A61B 6/06 | |
| 2005/0220265 A1 | 10/2005 | Besson | | |
| 2005/0243422 A1 | 11/2005 | Distler et al. | | |

(56) References Cited

U.S. PATENT DOCUMENTS

| | | | |
|---|---|---|---|
| 2008/0144775 | A1 | 6/2008 | Ramsauer et al. |
| 2008/0198963 | A1 | 8/2008 | Spahn |
| 2010/0119035 | A1 | 5/2010 | Karch |
| 2013/0287179 | A1 | 10/2013 | Fadler et al. |

FOREIGN PATENT DOCUMENTS

| | | |
|---|---|---|
| CN | 103377745 A | 10/2013 |
| DE | 10244898 A1 | 4/2004 |
| DE | 102008056891 B4 | 4/2012 |
| JP | H073601 U | 1/1995 |
| KR | 20120013724 A | 2/2012 |
| WO | WO 2012018188 A3 | 5/2012 |
| WO | WO 2012168832 A1 | 12/2012 |

OTHER PUBLICATIONS

Chinese Office Action and English translation thereof dated Mar. 3, 2017.
International Search Report dated Mar. 3, 2015.
German Office Action dated Sep. 25, 2014.

\* cited by examiner

US 10,123,756 B2

SINGLE SOURCE DUAL ENERGY HAVING TWO FILTERS FOR X-RAY SPECTRUM DIFFERENTIATION IN THE CASE OF RADIATOR SCREENS HAVING SLOTTED PLATES

PRIORITY STATEMENT

This application is the national phase under 35 U.S.C. § 371 of PCT International Application No. PCT/EP2015/051962 which has an International filing date of Jan. 30, 2015, which designated the United States of America and which claims priority to German patent application number DE 102014202330.0 filed Feb. 10, 2014, the entire contents of which are hereby incorporated herein by reference.

FIELD

An embodiment of the invention generally relates to a slotted plate, a radiator screen including a slotted plate and/or an X-ray radiator for generating a fan beam. An embodiment of the invention further relates to a computed tomography device having such an X-ray radiator and/or to a method for controlling such a computed tomography device

BACKGROUND

In clinical application, computed tomography devices are used to acquire data records for an X-ray image which can be a specific material within an object to be examined or a patient. The aspect of material determination is becoming ever more important in routine clinical problems and so the importance and field of application of computed tomography devices has greatly increased.

A computed tomography device used to recognize material during the evaluation and display of X-ray data operates on the principle of the so-called dual energy method. In this method, the object to be examined or the patient is, for example, scanned with X-quanta up to 80 keV and with X-ray quanta up to 140 keV. As a result of the different X-ray spectra of the two types of X-ray radiation, a different average attenuation is generated such that more comprehensive information is gathered compared to a conventional computed tomography device in normal operation.

In this context, it is either possible for two X-ray radiators with different energy to be used during a scan or for the tube voltage of an X-ray radiator to be alternated between two scans or positions of the X-ray radiator executed directly one after the other. The different tube voltage of the two scans results a change to the X-ray spectrum required for the dual-energy method.

This change to the X-ray spectrum can also be intensified by an X-ray filter arranged in the beam path during one of the two scans or positions. A further alternative consists in the at least partial attenuation of the X-ray radiation with a given energy from an X-ray source by the selective use of an X-ray filter in the beam path of the X-ray source in order to generate X-ray radiation with variable energy. In addition to a software expansion, an alternative of this kind also requires the expansion of the hardware of the computed tomography system, wherein a separate moving mechanism is required for moving and positioning the X-ray filter. For example, US 2008/0198963 A1 and US 2005/0220265 A1 disclose X-ray systems for dual energy visualization in which a rotating X-ray filter can be positioned in the X-ray beam such that the spectrum of the X-ray radiation changes over time as a result of the rotation of the X-ray filter. Here, recordings are made alternately for each position, wherein each of the recordings corresponds to a different X-ray spectrum.

A slotted plate for limiting and shaping an X-ray fan beam is known from the U.S. Pat. No. 4,277,685 A, comprising several slotted openings with respectively different X-ray filtering regions for differentiating the X-ray spectrum of an incident X-ray beam, wherein the X-ray filtering regions in the area of the slotted openings are fixedly arranged.

A slotted plate is known from the DE 102 44 898 A1 for limiting and shaping an X-ray fan beam, said plate comprising several slotted openings with respectively different slot widths.

SUMMARY

An embodiment of the invention includes carrying out a dual-energy method.

An embodiment is directed to a slotted plate, a radiator screen with slotted plate, an X-ray radiator for generating a fan beam, a computed tomography device and a method. Advantageous developments of embodiments of the invention are described in the respective claims.

An embodiment of the invention in particular relates to a slotted plate for a radiator screen for limiting an incident X-ray beam with at least one first slotted opening and comprising two different X-ray filter regions for the X-ray spectrum differentiation of the incident X-ray beam, wherein the two different X-ray filter regions are permanently arranged in the region of the at least one first slotted opening such that radiation components of the X-ray beam penetrating the at least one first slotted opening having different X-ray spectra can be generated simultaneously.

An embodiment is directed to a radiator screen for generating a fan beam including a slotted plate according to an embodiment of the invention.

An embodiment of the invention is also directed to an X-ray radiator for generating a fan beam comprising at least one X-ray radiation source and a radiator screen with a slotted plate according to an embodiment of the invention arranged downstream of the X-ray source and with respect to the X-ray source. Here, the slotted plate comprises at least one slotted opening with two different X-ray filter regions for X-ray spectrum differentiation and can be positioned in the beam path of the X-ray source such that radiation components of the fan beam with different X-ray spectra can be generated simultaneously. The advantages and preferred embodiments cited with reference to the slotted plate can be applied analogously to the X-ray radiator.

An embodiment of the invention is also directed to a computed tomography device for carrying out a scan, for example a spiral scan or a sequential scan, comprising a rotatable X-ray radiator according to an embodiment of the invention for generating a fan beam and an X-ray detector positioned diametrically opposite thereto with an assigned evaluating unit.

Finally, an embodiment of the invention relates to a method for controlling a computed tomography device, wherein the computed tomography device comprises a rotatable X-ray radiator for generating a fan beam and an X-ray detector positioned diametrically opposite thereto with an assigned evaluating unit, wherein two different X-ray filter regions are arranged downstream of the X-ray radiation source by the appropriate positioning of a slotted opening of a slotted plate of a radiator screen that can be moved with respect to the X-ray radiation source, the different X-ray filter regions enable different radiation components of a fan beam to be embodied simultaneously, wherein the radiation components comprise different X-ray spectra and the measuring signals of the different radiation components for obtaining dual-energy recordings are recorded simultaneously and evaluated separately.

BRIEF DESCRIPTION OF THE DRAWINGS

The invention will be described once again in more detail below with reference to the attached figures and example embodiments by way of example. Here, the same components are provided with identical reference numbers in the different figures. The depictions in the figures are schematic and greatly simplified and not necessarily true to scale. The figures show.

DETAILED DESCRIPTION OF THE EXAMPLE EMBODIMENTS

Figure 1:
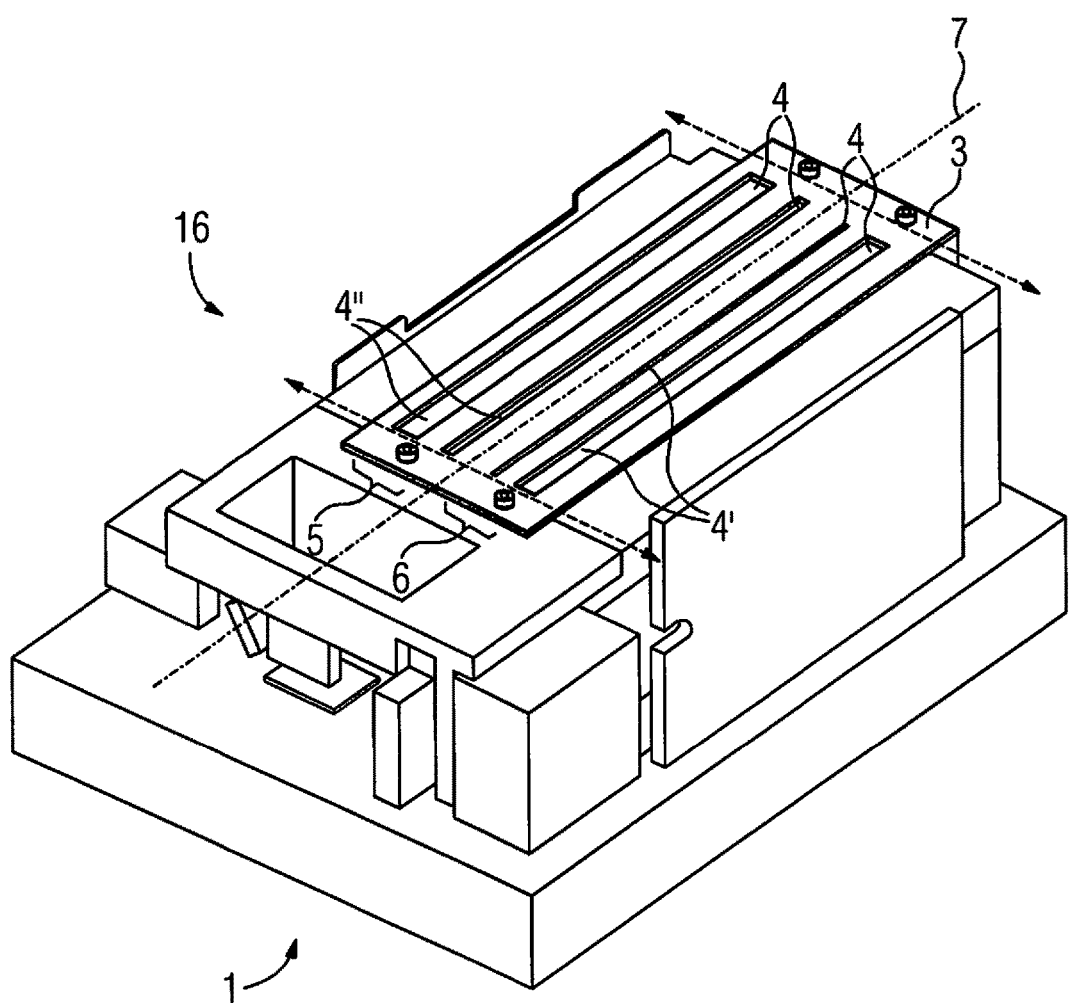
FIG. 1 a perspective view of a radiation screen according to an embodiment of the invention with a slotted plate, FIG. 2 a front view of a computed tomography device in normal operation, FIG. 3 a front view of the computed tomography device according to FIG. 1 in dual-energy operation, FIG. 4 a side view of a computed tomography device in normal operation, FIG. 5 a side view of the computed tomography device according to FIG. 4 in dual-energy operation, FIG. 6 a side view of a slotted plate according to an embodiment of the invention with an X-ray filter arrangement in a region of the slotted plate, FIG. 7 a top view of a slotted plate according to an embodiment of the invention with a first arrangement of the filter regions, FIG. 8 a top view of a further slotted plate according to an embodiment of the invention with a second arrangement of the filter regions, FIGS. 9 to 12 a perspective view further slotted plate according to an embodiment of the invention, FIG. 13 a diagram of the X-ray spectrum of an unfiltered X-ray radiation, and FIG. 14 a diagram of the X-ray spectrum of an X-ray radiation filtered through two different filter regions.

An embodiment of the invention in particular relates to a slotted plate for a radiator screen for limiting an incident X-ray beam with at least one first slotted opening and comprising two different X-ray filter regions for the X-ray spectrum differentiation of the incident X-ray beam, wherein the two different X-ray filter regions are permanently arranged in the region of the at least one first slotted opening such that radiation components of the X-ray beam penetrating the at least one first slotted opening having different X-ray spectra can be generated simultaneously.

An embodiment of the invention is based on the consideration that an X-ray filter can be used to attenuate the X-ray radiation from a single X-ray source such that its X-ray spectrum is changed relative to that of the unfiltered X-ray radiation. This enables a change to the X-ray spectrum be generated or intensified.

An embodiment of the invention is further based on the consideration that, with the aid of at slotted plate having at least one slotted opening that can be moved relative to the X-ray source and with at least one X-ray filter permanently arranged on the slotted plate, a radiator screen particularly favorably enables such a change to the X-ray spectrum to be implemented in a material-saving way and in a simple embodiment.

An embodiment of the invention is further based on the consideration that different filter materials change the X-ray spectrum of X-ray radiation in different ways and that the use of two different X-ray filters or two different X-ray filter regions enables two radiation components with different X-ray spectra to be generated simultaneously such that the recording of the information required for dual energy recording can be obtained by way of a single scan, in particular a spiral scan in a technically simple manner.

Conventional computed tomography devices are as a rule equipped with a so-called radiator screen with a slotted plate which shapes the fan beam and which can be used to set a defined slice thickness of a scan to be performed. In this case, an expansion to the radiator screen is relatively simple to implement from a technical viewpoint. The radiator screen or the slotted plate are simple to replace thus also enabling existing standard computed tomography devices to be retrofitted with a slotted plate according to the invention or with a radiation screen according to the invention for dual-energy recordings. In this way, the suggested solution represents a material-saving and simple embodiment characterized by a particularly inexpensive implementation.

In this context, X-ray radiation should be understood to mean the radiation which is produced from a tube voltage applied between an anode and a cathode in the X-ray radiator and emitted by the X-ray radiator in the form of a fan beam. This X-ray radiation has a spectrum with a maximum in keV corresponding to the maximum of the tube voltage in kV. The use of the two different X-ray filter regions result so-to-speak in the presence of two contiguous partial fan beams, namely two differently filtered radiation components of the incident fan beam comprising different X-ray spectra and which penetrate the patient simultaneously and are then detected by the X-ray detector.

The generation of the two radiation components takes place via the positioning of the slotted plate by the radiator screen, and hence the X-ray filter regions, in the beam path of the X-ray source. Here, in each case, one X-ray filter region only partially covers the fan beam. The respective radiation components comprise filtered X-ray radiation with an X-ray spectrum that has changed relative to the unfiltered, i.e. incident, X-ray radiation. The change to the X-ray spectrum is determined by the embodiment of the respective X-ray filter region, in particular the filter material used and the thickness of the filter material to be penetrated by the X-ray radiation.

Since the arrangement and the dimensions of the respective X-ray filter regions and the dimensions of the slotted plate are known, the image data recorded by the X-ray detector can be assigned to the two partial fan beams. This assignment obtains two data records with a specific information content, which can in particular be used to determine the penetrated tissue or material, from a scan with an X-ray radiator comprising such a radiator screen with slotted plate.

One substantial advantage when using such a radiator screen is the fact that the X-ray radiation source for generating the two radiation components does not have to be switched over, instead it can always be operated with the same tube voltage during the examination of the patient. The suggested solution for obtaining dual-energy recordings is also particularly favorable since there is no need for duplicate components of the computed tomography device, such as, for example, two X-ray radiators operated with different X-ray voltages or two X-ray detectors.

In addition, the radiator screen can be used to retrofit conventional computed tomography devices in that the radiator screen having the slotted plate according to the invention of the X-ray radiator used, which is used to form the desired scan slice thickness of the incident X-ray beam, is merely replaced and the different image records of different X-ray spectra are taken into account during the evaluation of the detector data. The suggested method for obtaining dual-energy recordings by the simultaneous filtering of incident X-ray radiation with two different X-ray filter regions converts a single-source computed tomography device into a dual-energy scanner in a simple way and will enable dual-energy recordings to become established on a broad scale in everyday clinical practice.

With respect to a particularly accurate evaluation of the data obtained by the X-ray detector, the arrangement and the dimensions of the X-ray filter regions and the position of the X-ray radiator are preferably correlated with that of the X-ray detector such that, during the evaluation, there is an assignment to those sub-areas of the X-ray detector which are impacted by the respective radiation components.

According to an advantageous development of the slotted plate according to an embodiment of the invention, the first X-ray filter region covers a first subarea of the at least one first slotted opening and the second X-ray filter region covers the remaining subarea of the at least one first slotted opening. Hence, altogether, the two X-ray filter regions cover the entire area of the at least one first slotted opening. This ensures that the detector surface area, which is used for data recording according to the dimensions of the at least one first slotted opening, is completely used. This also ensures that it is clear at all times which partial radiation component strikes which partial detector surface area. This ensures the assignment of the image data of an X-ray spectrum.

In other words, in this case, the X-ray filter regions of the radiator screen altogether cover the entire area of the slotted opening. As a result, when the slotted opening is appropriately arranged in the beam path of the X-ray source, the X-ray filter regions cover the complete desired region of the X-ray detector in two defined directions of extension of the X-ray detector. Here, the directions of extension are the φ-direction of the X-ray detector, i.e. the longitudinal direction of the X-ray detector and the Z-direction, i.e. the transverse direction of the X-ray detector. The region of the detector used is defined by the dimensions of the slotted opening selected and is therefore known.

Advantageously, in this case one of the two X-ray filter regions covers half the slotted width or half the slot length of the at least one first slotted opening. Particularly preferably, the other X-ray filter region covers the other half slotted width or the other half slot length of the at least one first slotted opening. With appropriate positioning of the slotted plate of a radiator screen with respect to the X-ray radiation source, and hence the X-ray filter regions, it is ensured that one half of the detector is available for the recording of a first partial fan beam with a first X-ray spectrum and the other half of the detector is available for the recording of the second partial fan beam with a second X-ray spectrum different from the first X-ray spectrum.

According to an advantageous development of the slotted plate according to an embodiment of the invention, the slotted plate additionally comprises at least one further slotted opening without an X-ray filter region, i.e. no X-ray filter region is assigned to the at least one further slotted opening. Hence, it is ensured that the same radiator screen can also be used to perform a normal mode of the computed tomography device. This simultaneously ensures that the same radiator screen can also be used to perform a dual-energy method with a single X-ray source, which is operated in a two-tube voltage mode. This has the advantage of enabling a simple comparison of dual-energy recordings, which were recorded in two different dual-energy recording modes but with the same device.

According to a further advantageous development of the slotted plate according to an embodiment of the invention, the dimensions of the at least one further slotted opening without an X-ray filter region and the dimensions of the at least one first slotted opening with two different X-ray filter regions are identical. This further simplifies the comparison between image recording in a normal mode and/or image recording in at least one of the dual-energy modes that can be performed.

According to a further advantageous development of the slotted plate according to an embodiment of the invention, the slotted openings are of different types, i.e. slotted openings with and without X-ray filter regions with the same dimensions are arranged next to one another. In other words, at least one further slotted opening without a filter region on the one hand and at least one first slotted opening with X-ray filter regions on the other are arranged next to one another. Advantageously, all slotted openings of different types are arranged in this manner. Here, the distance between two slotted openings with the same dimensions with and without filter regions is preferably identical for each coherent pair of slotted openings.

According to a further advantageous development of the slotted plate according to an embodiment of the invention, the slotted openings with and without X-ray filters are arranged separately in two different regions of the slotted plate. In other words, slotted openings with the same dimensions but of a different type, i.e. the slotted openings without a filter on the one hand and the slotted openings with an X-ray filter on the other, are in each case arranged in two different regions of the slotted plate. For example, the slotted plate has a first and a second region, which are arranged one below the other in a direction perpendicular to the longitudinal direction of the slotted plate. For example, at least all the slotted openings which do not have any X-ray filter are arranged in the first region and at least all slotted openings, which do have an X-ray filter are arranged in the second region of the slotted plate.

In one particular embodiment, the respective X-ray filters are embodied as a one-piece X-ray filter arrangement, which completely covers one of the two regions of the slotted plate and to be precise the region in which at least all slotted openings having at least one X-ray filter region are arranged. Here, the X-ray filter arrangement is positioned and secured with respect to the slotted plate and such that the respective slotted openings are covered in a defined manner by two X-ray filters with different properties. This simplifies the production of the X-ray filter arrangement and the assembly of the slotted plate for the radiator screen. Here, the distance between two slotted openings with the same dimensions with and without filters is preferably identical for each pair of slotted openings. Alternatively, the pairs in the different regions are arranged symmetrically around the boundary between the two regions. The boundary between the two different regions is, for example, the center line of the slotted plate in the longitudinal direction.

According to a further advantageous development of the slotted plate according to an embodiment of the invention, the at least one first slotted opening and the at least one further slotted opening are arranged together in a slotted plate.

According to a further advantageous development of the slotted plate according to an embodiment of the invention, the two different X-ray filter regions of the at least one first slotted opening comprise different materials. Here, at least one first X-ray filter comprises at least tin, aluminum, copper, titanium, tungsten, gold, Teflon, carbon, molybdenum and/or graphite. Alternatively, a first and a second X-ray filter optionally in each case consist of tin, aluminum, copper, titanium, tungsten, gold, Teflon, carbon, molybdenum or graphite, wherein the first and the second X-ray filter region, or X-ray filter regions, comprise a different filter material and/or filter material combinations and/or filter material thicknesses. In particular, the respective X-ray filters are suitable for filtering out low-energy X-ray radiation. Here, low-energy X-ray radiation should in particular be understood to be the X-ray spectrum up to the maximum intensity of the emitted, unfiltered, bremsstrahlung. Here, so-called hardening of the X-ray radiation takes place, i.e. all the X-ray radiation is attenuated, wherein this attenuation acts more intensively on the low-energy component and hence results in a greater component of the high-energy X-ray radiation in the distribution in the X-ray spectrum.

Alternatively or supplementarily, it is possible to set the desired properties of the X-ray filter by a suitably selected thickness of the filter material. In addition, the respective X-ray filter regions can also have two or more layers, i.e. they can consist of two or more layers with different compositions that form one filter unit in that they are arranged one on top of the other in the direction of radiation such that they are penetrated by X-rays one after the other. A defined change to the X-ray spectrum compared to unfiltered radiation is effected in dependence on the respective embodiment of the X-ray filter region (material, thickness, etc.).

According to a further advantageous development of the slotted plate according to an embodiment of the invention, the slotted plate comprises at least two slotted openings each with two X-ray filter regions arranged in the region of the respective slotted openings, wherein the two X-ray filter regions of the one and the other slotted opening have a different filter material combination. For example, a first slotted opening comprises two X-ray filter regions, wherein the first X-ray filter region comprises tin and the second X-ray filter region comprises graphite, while the further first slotted opening also comprises two X-ray filter regions, wherein the first X-ray filter region comprises tin with a different or the same thickness and the second X-ray filter region comprises gold. This enables image recordings to be generated in dual-energy methods with different X-ray spectrum combinations, possibly without changing the X-ray voltage. Here, the two slotted openings preferably have the same dimensions. This enables or simplifies a comparison between two dual-energy image recordings with different properties.

The different properties of the dual-energy image recordings enable more comprehensive, material-specific information to be obtained. Therefore this in particular enables further specific dual-energy fields of application to be covered. Advantageously, X-ray filter regions of the at least one first slotted opening comprise one of the following filter material combinations: tin/gold, tin/carbon, tin/graphite or tin/Teflon, while the X-ray filter regions of at least one other slotted opening comprise one of the other combinations from this group.

According to a further advantageous development of the slotted plate according to an embodiment of the invention, the slotted plate comprises at least one additional slotted opening with a single X-ray filter, preferably made of tin, which is permanently arranged in the region of the at least one further slotted opening. Preferably, the additional X-ray filter covers the entire area of the additional slotted opening. This additionally enables further complementary dual-energy methods to be performed, in particular in combination with one of the slotted openings without a filter or in combination with a radiation source that switches between two tube voltages.

Alternatively, the additional X-ray filter only partially covers the area of the slotted opening, for example only half of one of the two or both directions of extension ($\varphi$, Z). Preferably, the filter can also comprise at least tin, aluminum, copper, titanium, tungsten, gold, Teflon, carbon and/or graphite. This in turn enables further combinations of X-ray spectra by means of which still further material-specific information can be obtained and compared with other scans. This in particular enables further specific dual-energy fields of application to be covered.

According to a further advantageous development of the slotted plate according to an embodiment of the invention, the X-ray filter regions of the at least one slotted opening or the respective slotted openings are embodied as single filters. Alternatively, the X-ray filter regions of the at least one slotted opening or the respective slotted openings are embodied as an X-ray filter arrangement with adjacent regions with different filter properties.

An embodiment is directed to a radiator screen for generating a fan beam including a slotted plate according to an embodiment of the invention.

In an embodiment, the slotted plate of the radiator screen comprises a first and a further slotted opening and the slotted plate can be moved such that optionally the first slotted opening or the further slotted opening can be positioned in a beam path of the radiator screen prespecified by the radiator screen to generate the fan beam.

It is further preferable for a radiation-opaque region to be provided on the slotted plate. Moving the slotted plate such that the radio-opaque region is positioned in the beam path of the radiator screen prespecified by the radiator screen ensures that no radiation the leaves the screen ("switching off" the radiation by closing the radiator screen).

An embodiment of the invention is also directed to an X-ray radiator for generating a fan beam comprising at least one X-ray radiation source and a radiator screen with a slotted plate according to an embodiment of the invention arranged downstream of the X-ray source and with respect to the X-ray source. Here, the slotted plate comprises at least one slotted opening with two different X-ray filter regions for X-ray spectrum differentiation and can be positioned in the beam path of the X-ray source such that radiation components of the fan beam with different X-ray spectra can be generated simultaneously. The advantages and preferred embodiments cited with reference to the slotted plate can be applied analogously to the X-ray radiator.

An embodiment of the invention is also directed to a computed tomography device for carrying out a scan, for example a spiral scan or a sequential scan, comprising a rotatable X-ray radiator according to an embodiment of the invention for generating a fan beam and an X-ray detector positioned diametrically opposite thereto with an assigned evaluating unit.

In an embodiment, the position of the X-ray radiator is correlated with the position of the X-ray detector such that the corresponding positioning of the slotted plate of the radiator screen and hence of the X-ray filter regions or the filter arrangement with respect to the X-ray source of the X-ray radiator enables the simultaneous generation of two partial fan beams with different X-ray spectra that impact different partial regions of the X-ray detector thus enabling an assignment between the data recorded by the respective sub-areas of the X-ray detector and the associated partial fan beam with a specific X-ray spectrum. The evaluating unit is further embodied to evaluate the measuring signals of the different radiation components or the partial fan beam for obtaining dual-energy recordings separately of one another.

The advantages and preferred embodiments listed with respect to the radiator screen, slotted plate and X-ray radiator can be transferred analogously to the computed tomography device and to embodiments of the following method for controlling the computed tomography device.

In a further advantageous development of the computed tomography device according to an embodiment of the invention, the position of the different X-ray filter regions is correlated with that of the X-ray detector such that, during the evaluation, the sub-areas of the X-ray detector on which the different radiation components impact are assigned.

In a further advantageous development of the computed tomography device according to an embodiment of the invention, the first X-ray filter region covers a first prespecified sub-area of the X-ray detector and the second X-ray filter region covers a second prespecified sub-area of the X-ray detector in defined directions of extension ($\varphi$, Z) of the X-ray detector.

In an embodiment, the computed tomography device can be operated in normal operation without X-ray filters and in a dual-energy mode with or without X-ray filters and/or X-ray filter regions. In particular, the computed tomography device can be operated in a normal and dual-energy mode with a sequential scan or spiral scan.

Finally, an embodiment of the invention relates to a method for controlling a computed tomography device, wherein the computed tomography device comprises a rotatable X-ray radiator for generating a fan beam and an X-ray detector positioned diametrically opposite thereto with an assigned evaluating unit, wherein two different X-ray filter regions are arranged downstream of the X-ray radiation source by the appropriate positioning of a slotted opening of a slotted plate of a radiator screen that can be moved with respect to the X-ray radiation source, the different X-ray filter regions enable different radiation components of a fan beam to be embodied simultaneously, wherein the radiation components comprise different X-ray spectra and the measuring signals of the different radiation components for obtaining dual-energy recordings are recorded simultaneously and evaluated separately.

FIG. 1 is a schematic display of an X-ray radiator 1 according to an embodiment of the invention with a radiator screen 16 comprising a slotted plate 3. An X-ray radiator 1 with an X-ray radiation source 2 (not shown) is assigned to the radiator screen 16. The radiator screen 16 comprises a screen with internal sensors for determining the focus and measuring the dose of the X-ray radiation source 2 (not shown) and, at the beam exit of the radiator screen 16, a slotted plate 3 that can be moved with respect to the X-ray radiation source 2. The screen box is used for shielding and the first limiting of the X-ray fan beam. Further X-ray filters (not shown) for shaping the fan beam and further elements for limiting the fan beam can be arranged in the screen box.

The slotted plate 3 has a plate-like shape and in this example four slotted openings 4 for further limiting the fan beam. Here, a slotted opening 4 can have a rectangular profile, however, alternatively, the lateral edges of the slotted opening 4 could also have a different geometry, in particular, for example, it can be concavely or convexly arched. Hence, the slotted plate 3 has a shaping and limiting effect on the fan beam. The slotted plate 3 is made of a material which is substantially impermeable to X-rays, for example a tungsten composite.

The X-ray radiator 1 comprises as an X-ray radiation source 2 (which is not shown in further detail here) a cathode and an anode arranged in a vacuum housing. An adjustable tube voltage of approximately 25 kV to approximately 150 kV is applied between the cathode and the anode. This tube voltage causes electrons emitted by the cathode to be accelerated toward the anode on which they then impact with a maximum energy of 25 keV to 150 keV. The impact of the electrons effects X-ray radiation that leaves the vacuum housing through a beam exit window and is shaped by the radiator screen 16 and the slotted plate 3 in the style of a fan beam.

The X-ray radiation has a power distribution with a maximum energy in kilo-electron volts that is numerically equal to the tube voltage applied between the cathode and the anode in kilovolts. Therefore, with a tube voltage of, for example, 140 kV, the maximum X-ray radiation has an energy of 140 keV. However, the greatest part of the X-ray radiation is in an energy range of approximately half up to $\tfrac{2}{3}$rds of the tube voltage.

In the example shown here, in each case two slotted openings 4 with a different width are arranged in a first region 5 and in a second region 6 of the slotted plate 3, wherein the two regions 5, 6 are adjacent to one another in the longitudinal direction 7 on the center line of the slotted plate 3. In this example, the two slotted openings 4' in the second region 6 have an X-ray filter arrangement 8 extending over the second region 6 (see FIG. 6) having regions with different filter properties. Here, these regions are embodied in the x-ray filter arrangement 8. The x-ray filter arrangement 8 is arranged such with respect to the slotted openings 4 that each slotted opening 4' has two different X-ray filter regions. The radiation passing through these slotted openings 4' is attenuated such that, after passing through the respective slotted opening 4', the incident radiation fan beam 14 is split into adjacent partial radiation fan beams 14a, 14b with different X-ray spectra (see FIGS. 3 and 5).

The slotted plate 3 can be moved linearly along the transverse direction, i.e. perpendicular to the longitudinal direction 7 of the slotted plate 3. The travel path of the slotted plate 3 is indicated by the dashed lines with arrows and depicts the Z-direction. This enables a specific slotted opening 4 to be optionally arranged in the beam path of the X-ray radiation source 2. The different slotted openings 4 enable CT scans with different slice widths to be taken.

Figure 2:
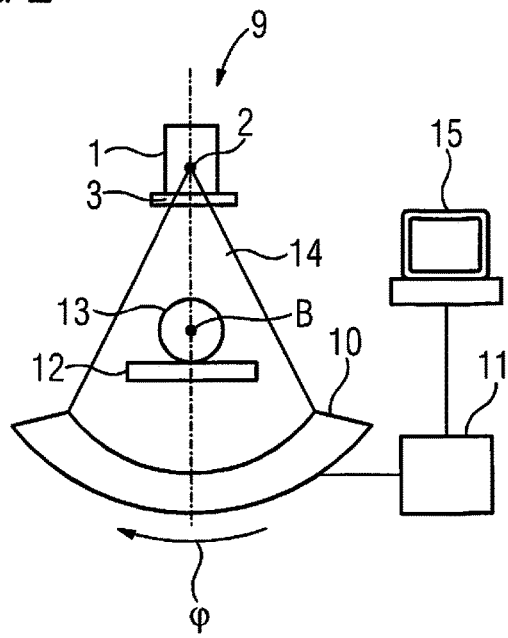

FIG. 2 is a schematic front view of a computed tomography device 9 in normal operation, which, in the example embodiment shown, comprises an X-ray radiator 1 with an X-ray radiation source 2 and a radiator screen 16 (not shown) arranged before the X-ray radiation source 2 with which the slotted plate 3 of the radiator screen 16 can be moved in the Z-direction, i.e. transverse to the X-ray detector 10, an evaluating unit 11 and an X-ray detector 10 positioned diametrically opposite the X-ray radiator 1. In this variant, the X-ray filter regions 8a, 8b are arranged in the transverse direction (see FIG. 8) of the slotted openings 4.

The X-ray radiator 1 and the X-ray detector 10 are arranged rotatably about an axis B extending perpendicular to the plane of the drawing. A patient table 12 extends along the axis B such that, in operation, the components of the computed tomography device 9 rotate about a patient 13 mounted on the patient table 12. The rotation of the computed tomography device 9 is combined with the insertion of the patient table along the axis B thus enabling a spiral scan or a sequential scan of the patient 13 to be performed.

An X-ray filter arrangement 8 or X-ray filter regions 8a, 8b with different properties are installed in the radiator screen 16 having the slotted plate 3 in the region of at least one slotted opening 4'. The slotted plate 3 of the radiator screen 16 can be moved linearly in the Z-direction of the incident radiation fan beam 14 of the X-ray radiation source 2 of the X-ray radiator 1. The incident radiation fan beam 14 impacts the planar X-ray detector 10 which is embodied in a curved shape for the detection of the entire incident radiation fan beam 14 and extends in an φ-direction which coincides with the longitudinal direction of the X-ray detector 10 a Z-direction, indicating the transverse direction of the X-ray detector 10.

The X-ray detector 10 is connected by data technology to an evaluating unit 11 embodied to evaluate the measuring signals of the X-ray detector 10 such that the data records obtained can be used for the reconstruction of image data. In this context, the evaluating unit 11 is used, on the one hand, for the acquisition of measured data and, on the other, for the reconstruction of the image data. The image data is further processed on a workstation 15, which communicates with the evaluating unit 11.

Figure 3:
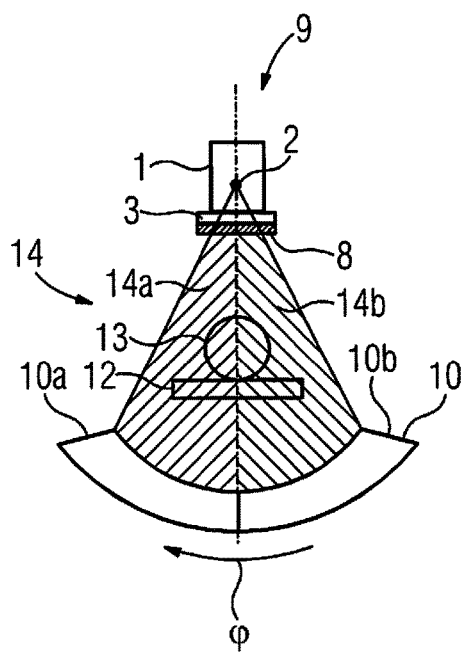

With appropriate positioning of the slotted plate 3 of the radiator screen as shown in FIG. 3 such that a slotted opening 4' with an X-ray filter arrangement 8 or X-ray filter regions 8a, 8b with different properties is positioned in the incident fan beam 14 of the X-ray source produces two radiation components 14a, 14b whose energy distribution lies within in two different energy ranges. The filtered radiation components 14a, 14b are indicated by differently hatched areas and have X-ray spectra that are restricted compared to unfiltered X-ray radiation 14. For example, a tube voltage of 140 kV is applied between the cathode and the anode.

Here, one of the two X-ray filter regions 8a, 8b is made of a metal such as, for example, tin, which attenuates the low-energy component of the X-ray radiation to a greater degree than the high-energy component. The X-ray radiation 14a filtered by this filter region 8a impacts a sub-area 10a of the X-ray detector 10. At the same time, the remaining sub-area 10b of the X-ray detector 10 measures a further signal of the X-ray radiation 14b filtered by the other filter region 8b. The evaluating unit 11 is embodied to evaluate the measuring signals from the two partial areas 10a, 10b separately from one another such that the two data records obtained can be used for the reconstruction of dual energy-image data. The reconstructed image data can then be further processed using methods that are already known for dual-energy processing. As a rule, this further processing takes place at application level at application level on the workstation 15.

Figure 4:
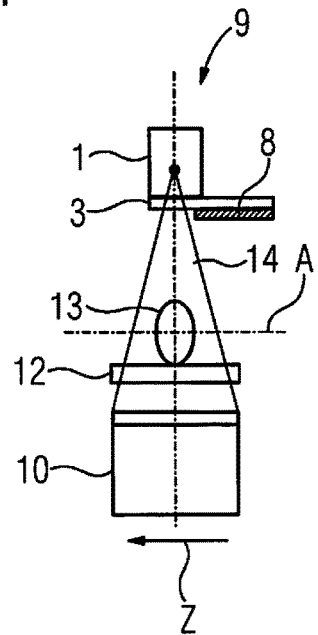
Figure 5:
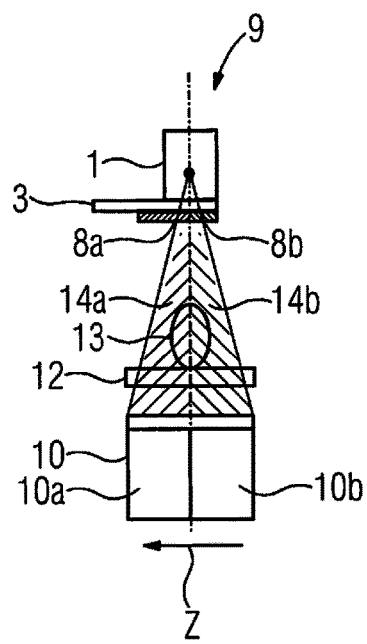

FIGS. 4 (normal mode) and 5 show a side view of a second variant of a computed tomography device 9 with which the X-ray filter arrangement 8 is arranged in the longitudinal direction (see FIG. 7) of the slotted openings 4. With appropriate positioning of the slotted plate 3 as shown in FIG. 5 such that a slotted opening 4' with an X-ray filter arrangement 8 or X-ray filter regions 8a, 8b with different properties is positioned in the incident fan beam 14 of the X-ray source, two radiation components 14a, 14b are produced whose energy distribution lies within two different energy ranges. As is evident from FIG. 5, the differently filtered radiation components 14a, 14b are measured simultaneously by the subareas 10a, 10b of the X-ray detector 10.

Figure 6:
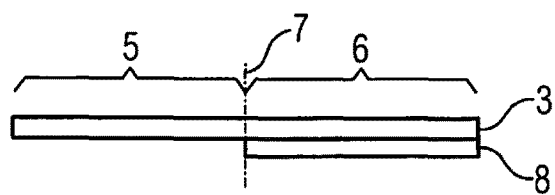

FIG. 6 is a schematic side view of the slotted plate 3. Here, the slotted plate 3 has a first region 5 and a second region 6 which are adjacent to one another at the center line of the slotted plate in the longitudinal direction 7. In the first region 5, the slotted openings 4" do not have an X-ray filter. In the second region 6, the slotted openings 4' comprise an X-ray filter arrangement 8 which extends over the entire second region 6 of the slotted plate 3. The X-ray filter arrangement 8 is permanently arranged on the slotted plate. The X-ray filter arrangement 8 is preferably arranged on the side of the slotted plate 3 facing the X-ray source 2. The X-ray filter arrangement 8 comprises at least two, (not shown in FIG. 6) X-ray filter regions 8a, 8b having different filter properties. In one example (not shown), the X-ray filter regions 8a, 8b extend individually only in the region of the respective slotted openings 4'.

Figure 7:
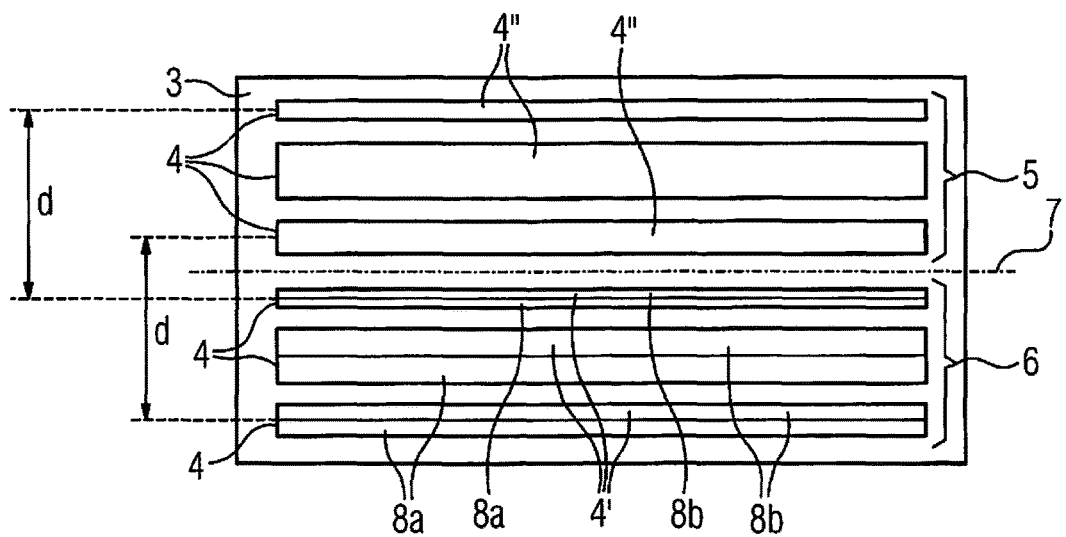
Figure 8:
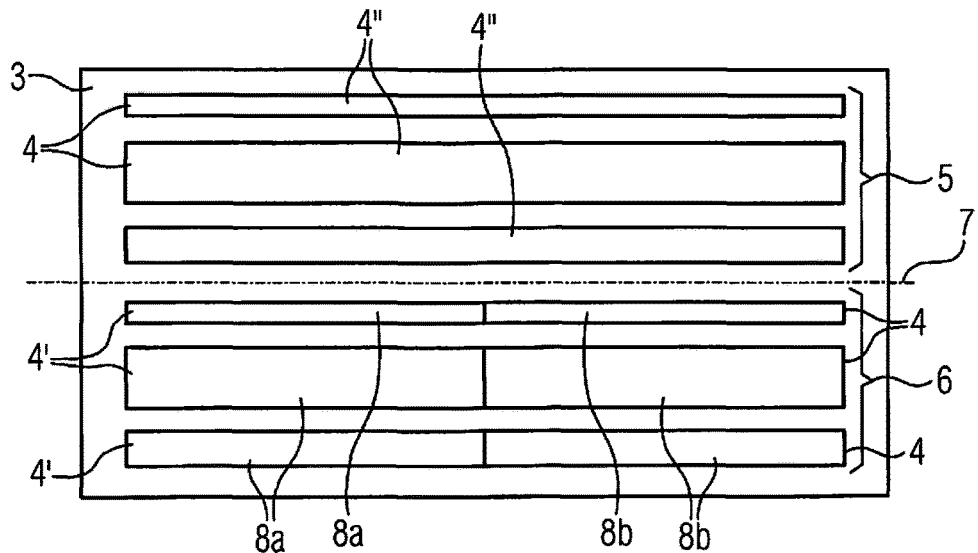

FIGS. 7 and 8 are schematic top view views of two different embodiments of a slotted plate 3 according to the invention. In this example, the slotted plate 3 has six slotted openings 4. Here, in each case two slotted openings have the same dimensions. Of these openings 4, three 4" are embodied without an X-ray filter region in the region of the slotted opening and are located in a first region 5 of the slotted plate 3. X-ray filter regions 8a, 8b are assigned to the remaining three slotted openings 4', which in each case cover the entire area of the individual three slotted openings 4'.

In the example shown, the arrangement and the dimensions of the slotted openings with filters 4' and without filters 4" are identical and only linearly displaced with respect to the center line 7 of the slotted plate in the longitudinal direction by a distance d. This makes the distance d between two slotted openings with the same dimensions with and without filters identical for each pair of slotted openings 4', 4".

In FIGS. 7 and 8, X-ray filter regions 8a and 8b with different filter properties are arranged in the region of the slotted openings 4'. Here, the total area spanned by the coherent X-ray filter regions covers the entire area of the respective slotted openings 4'. As shown in FIGS. 7 and 8, the respective X-ray filter regions 8a, 8b in each case cover half the area of the respective slotted openings. FIG. 7 shows a variant in which the individual X-ray filter regions 8a, 8b are arranged one under the other and parallel to the longitudinal direction of the slotted opening. FIG. 8 shows a further variant in which the individual X-ray filter regions 8a, 8b are arranged next to one another and perpendicular to the longitudinal direction of the slotted opening.

FIGS. 9 to 12 are perspective views of further slotted plates according to an embodiment of the invention for a radiation screen according to an embodiment of the invention.

Figure 9:
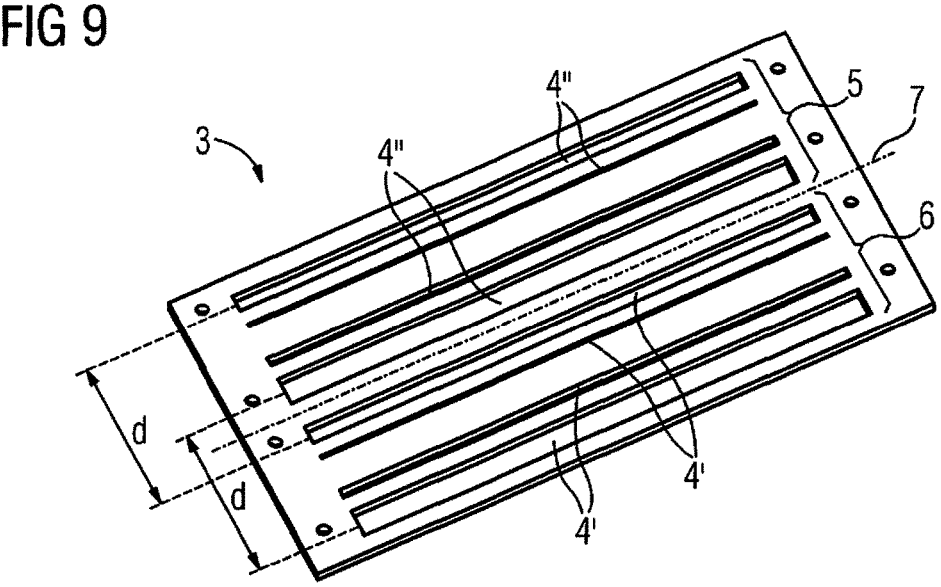

FIG. 9 is a schematic perspective view of a further embodiment of the slotted plate 3 according to the invention of a radiator screen. In this example, the slotted plate 3 has eight slotted openings 4. Here, in each case two slotted openings have the same dimensions. Of these openings 4, four 4" are embodied without an X-ray filter region and are located in a first region 5 of the slotted plate 3. X-ray filter regions are arranged in the remaining further four slotted openings 4' which cover the entire area of the four slotted openings 4'.

In one example (not shown) each slotted opening 4' comprises an individual X-ray filter 8 comprising two X-ray filter regions 8a, 8b with different properties, which together completely cover the area of the respective slotted opening. Here, the different X-ray filter regions 8a, 8b have different properties, in particular filter material combinations of the individual filter regions 8a and 8b. In the example shown, the arrangement and dimensions of the slotted openings with filters 4' and without filters 4" are identical and only linearly displaced with respect to the center line 7 of the slotted plate in the longitudinal direction by a distance d. This makes the distance d between two slotted openings with the same dimensions with and without filters identical for each pair of slotted openings 4', 4".

Figure 10:
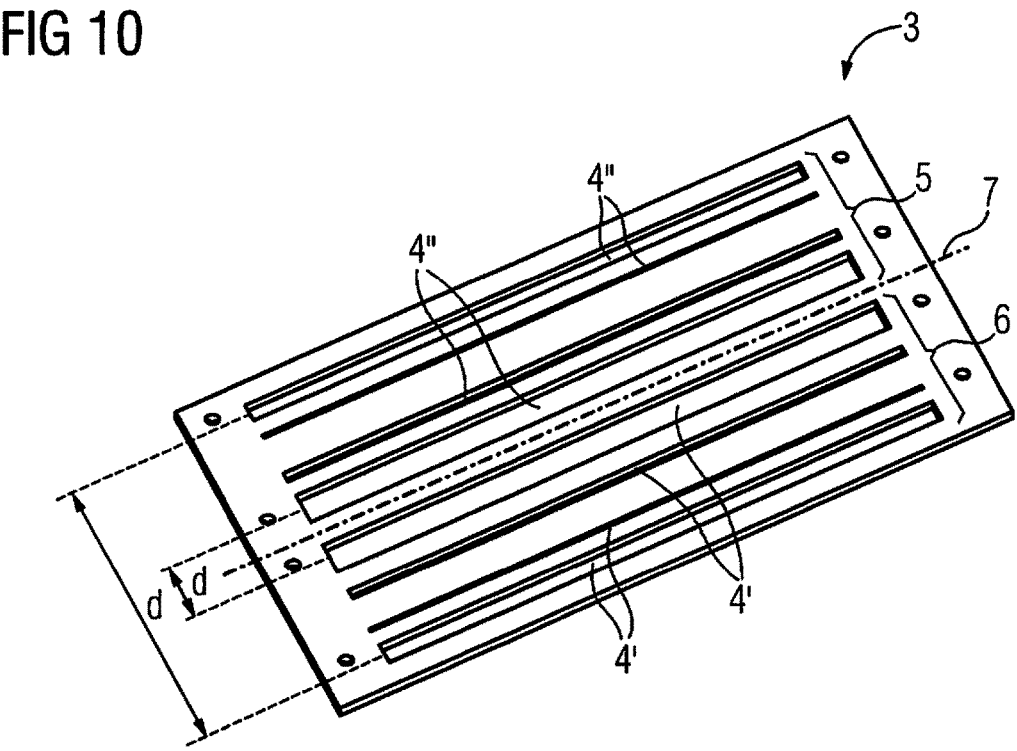

In FIG. 10, the arrangement and dimensions of the slotted openings 4 with filters 4' and without filters 4" are identical and only embodied symmetrically with respect to the center line 7 of the slotted plate in the longitudinal direction. This makes the distance d between two slotted openings with the same dimensions with and without filters greater toward the outside for each pair of slotted openings 4', 4".

Figure 11:
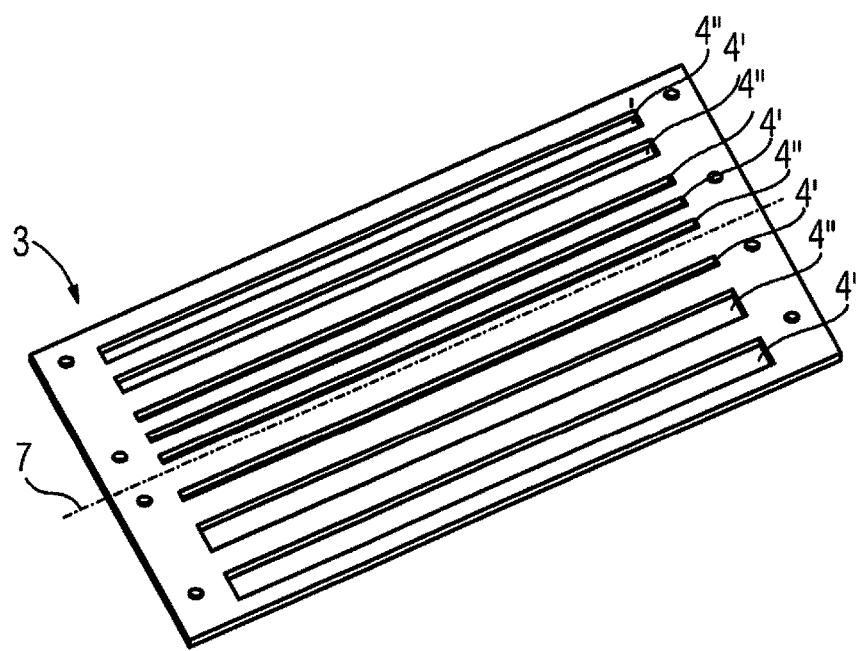

In FIG. 11, the distance between two slotted openings with the same dimensions with filters 4' and without filters 4" are selected as the same and a slotted opening 4" without filters and a slotted opening 4' with filter regions 8 are always arranged in pairs next to one another and in parallel to the longitudinal direction of the slotted plate 3.

Figure 12:
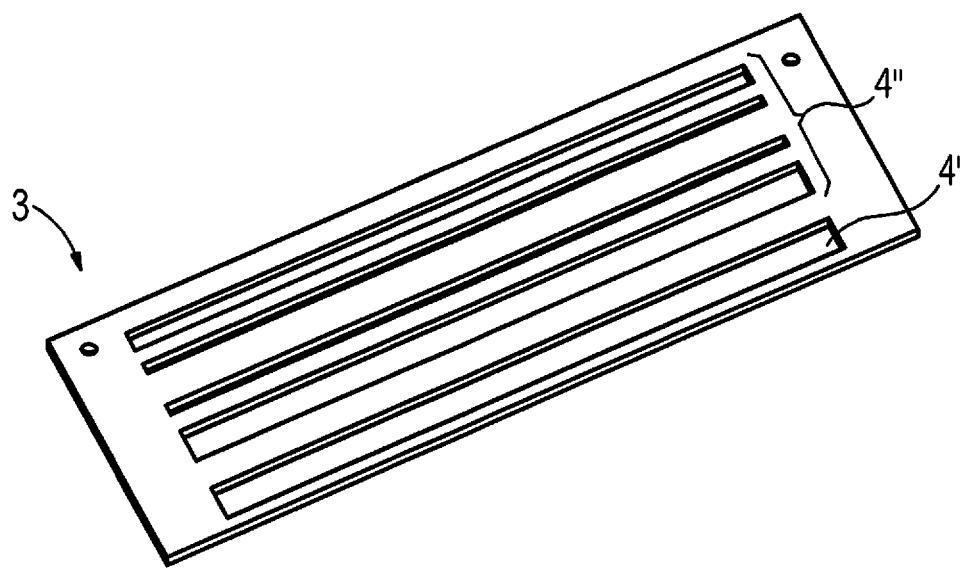

FIG. 12 shows another further embodiment of the slotted plate 3. The slotted plate 3 has an optional number of slotted openings 4. Here, at least the slotted openings without filters 4" have different dimensions such that different slice thicknesses can be selected for a scan. Moreover, the slotted plate 3 has at least two slotted openings 4' with filter regions 8, wherein the two filter regions 8 have different filter material combinations. The slotted openings 4' preferably have the same dimensions as one of the slotted openings 4" without filters. In a further example (not shown) of a further embodiment of the slotted plate 3 according to the invention of the radiator screen, the slotted plate 3 additionally or alternatively has a further slotted opening with a homogeneous filter region, for example made of tin, which completely covers a slotted opening 4.

Figure 13:
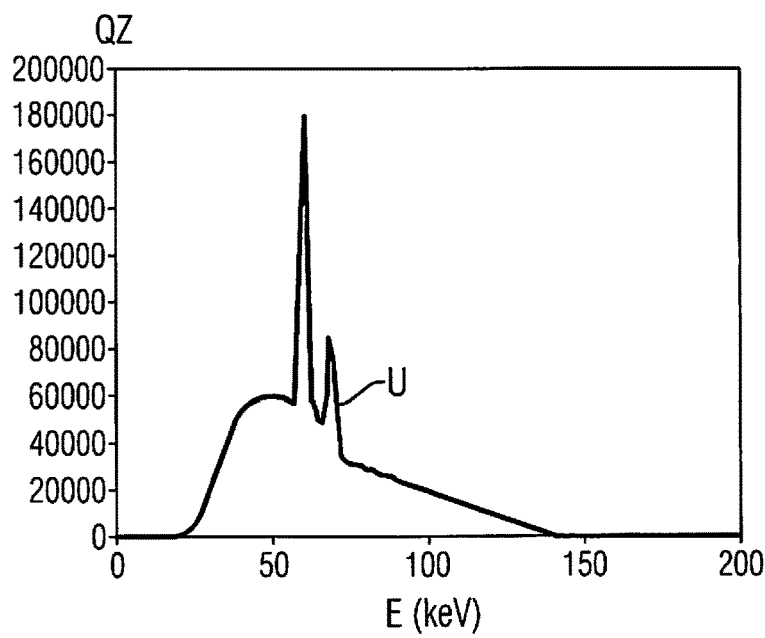
Figure 14:
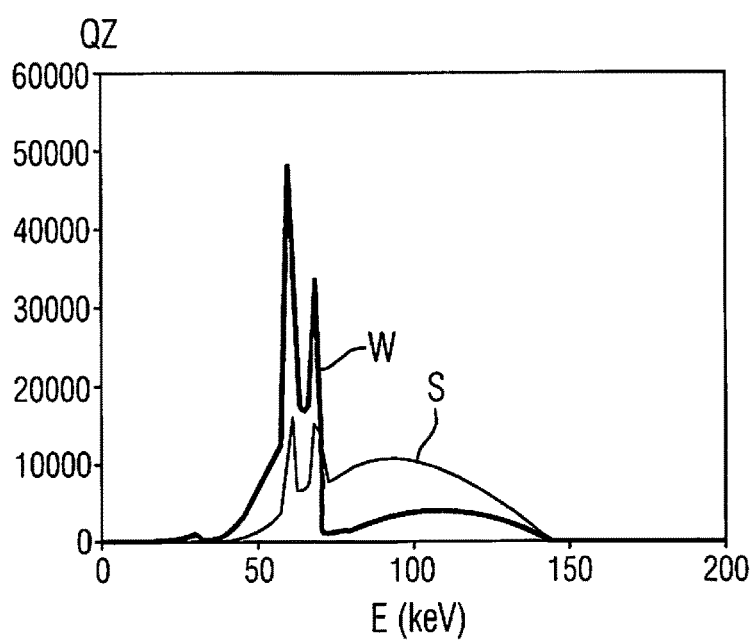

The impact of an X-ray filter region 8a, 8b on the spectrum of the X-ray radiation 14 is evident from FIGS. 13 and 14. In FIG. 13, the quantum number QZ is plotted over the energy distribution E of unfiltered X-ray radiation of 14 to 140 keV. Here, the peaks between 50 and 70 keV correspond to the characteristic X-ray radiation. FIG. 14 shows the X-ray spectra W and S after the X-ray radiation has been filtered through two different filters. Here, the X-ray filter materials used are tungsten (curve W) and tin (curve S). As is evident from this figure, filtering with such materials substantially effects the attenuation and above all a different distribution or course of the X-ray spectrum. These filter materials cause the low-energy X-ray radiation, i.e. the X-ray radiation up to the maximum intensity Imax of the unfiltered bremsstrahlung (the "hump" shortly before 50 keV in FIG. 13) to be markedly attenuated. These amended X-ray spectra (W, S) are used for the dual-energy evaluation.

The invention claimed is:

1. A slotted plate for limiting and shaping an X-ray fan beam, comprising:
   at least one first slotted opening; and
   two different X-ray filter regions for X-ray spectrum differentiation of an incident X-ray beam, the two different X-ray filter regions being permanently arranged in a region of the at least one first slotted opening such that radiation components of the incident X-ray beam penetrating the at least one first slotted opening including different X-ray spectra are simultaneously generatable; and
   at least one further slotted opening, wherein no X-ray filter region is arranged in a region of the at least one further slotted opening.

2. The slotted plate of claim 1, wherein a first of the two different X-ray filter regions covers a first subarea of the at least one first slotted opening and a second of the of the two different X-ray filter regions covers a remaining subarea of the at least one first slotted opening.

3. The slotted plate of claim 2, wherein each of the two different X-ray filter regions respectively covers half a slotted width of the at least one first slotted opening or half a slotted length of the at least one first slotted opening.

4. The slotted plate of claim 2, wherein the at least one first slotted opening includes at least two first slotted openings, each of the at least two first slotted openings including two different X-ray filter regions, wherein each of the two different X-ray filter regions of the at least two first slotted openings includes a different combination of filter materials.

5. The slotted plate of claim 1, wherein each of the two different X-ray filter regions respectively covers half the a slotted width of the at least one first slotted opening or half a slotted length of the at least one first slotted opening.

6. The slotted plate of claim 1, wherein dimensions of the at least one further slotted opening and dimensions of the at least one first slotted opening are identical.

7. The slotted plate of claim 6, wherein the at least one first slotted opening and the at least one further slotted opening are arranged next to one another.

8. The slotted plate of claim 7, wherein the at least one first slotted opening and the at least one further slotted opening are arranged separately in different regions of the two different X-ray filter regions.

9. The slotted plate of claim 6, wherein the at least one first slotted opening and the at least one further slotted opening are arranged separately in different regions of the two different X-ray filter regions.

10. The slotted plate of claim 1, wherein the at least one first slotted opening and the at least one further slotted opening are arranged separately in different regions of the two different X-ray filter regions.

11. The slotted plate of claim 1, wherein the two different X-ray filter regions of the at least one first slotted opening comprise different filter materials.

12. The slotted plate of claim 11, wherein the two different X-ray filter regions of the at least one first slotted opening include a combination of filter materials selected from the group of combinations consisting of tin/gold, tin/carbon, and tin/graphite.

13. The slotted plate of claim 1, wherein at least one X-ray filter region of the two different X-ray filter regions comprises a filter material selected from the group consisting of tin, aluminum, copper, titanium, tungsten, gold, carbon, molybdenum and graphite.

14. The slotted plate of claim 1, wherein the at least one first slotted opening includes at least two first slotted openings, each of the at least two first slotted openings including two different X-ray filter regions, wherein each of the two different X-ray filter regions of the at least two first slotted openings includes a different combination of filter materials.

15. The slotted plate of claim 1, wherein the two different X-ray filter regions comprise single X-ray filters or an X-ray filter arrangement with adjacent regions with different filter properties.

16. A radiator screen for generating an X-ray fan beam, comprising
the slotted plate of claim 1.

17. The radiator screen of claim 16, wherein the slotted plate further comprises a further slotted opening and wherein the slotted plate is movable such that the at least one first slotted opening is positionable in a beam path of the radiator screen prespecified by the radiator screen for generating the X-ray fan beam.

18. An X-ray radiator for generating an X-ray fan beam comprising:
an X-ray radiation source; and
the radiator screen of claim 16, arranged downstream of the X-ray radiation source, wherein the two different X-ray filter regions are arranged in a region of the at least one first slotted opening, for X-ray spectrum differentiation, the at least one first slotted opening being positionable in a beam path of the X-ray radiation source such that radiation components of the X-ray fan beam with different X-ray spectra are simultaneously generatable.

19. A computed tomography device comprising:
the X-ray radiator of claim 18 for generating an X-ray fan beam; and
an X-ray detector, positioned diametrically opposite the X-ray radiator.

20. The computed tomography device of claim 19, wherein an arrangement of the two different X-ray filter regions is correlated with an arrangement of the X-ray detector such that, during an evaluation, there is an assignment of sub-areas of the X-ray detector impacted by the different radiation components with different X-ray spectra.

21. The computed tomography device of claim 20, wherein a first X-ray filter region of the two different X-ray filter regions covers a first prespecified sub-area of the X-ray detector and a second X-ray filter region of the two different X-ray filter regions covers a second prespecified sub-area of the X-ray detector in defined directions of extension of the X-ray detector.

22. The computed tomography device of claim 19, wherein a first X-ray filter region of the two different X-ray filter regions covers a first prespecified sub-area of the X-ray detector and a second X-ray filter region of the two different X-ray filter regions covers a second prespecified sub-area of the X-ray detector in defined directions of extension of the X-ray detector.

23. The computed tomography device of claim 19, wherein an arrangement of the two different X-ray filter regions is correlated with an arrangement of the X-ray detector such that the two different X-ray filter regions, each of the two different X-ray filter regions respectively cover half of the X-ray detector.

24. The computed tomography device of claim 19, operatable in normal operation without an X-ray filter region of the two different X-ray filter regions and in a dual-energy mode with the two different X-ray filter regions.

25. A method for controlling the computed tomography device of claim 19, comprising:
generating an X-ray fan beam simultaneously comprising different radiation components, wherein the different radiation components comprise different X-ray spectra, and
separately evaluating measured signals of the different radiation components for obtaining dual-energy recordings.

26. A radiator screen for generating an X-ray fan beam, comprising the slotted plate of claim 2.

27. The radiator screen of claim 26, wherein the slotted plate further comprises a further slotted opening, wherein the slotted plate is movable such that the at least one first slotted opening is positionable in a beam path of an X-ray radiation source prespecified by the radiator screen for generating the X-ray fan beam.

28. A slotted plate for limiting and shaping an X-ray fan beam, comprising:
at least one first slotted opening; and
two different X-ray filter regions for X-ray spectrum differentiation of an incident X-ray beam, the two different X-ray filter regions being permanently arranged in a region of the at least one first slotted opening such that radiation components of the incident X-ray beam penetrating the at least one first slotted opening including different X-ray spectra are simultaneously generatable; and
at least one additional slotted opening including one single X-ray filter region permanently arranged at least partially in a region of the at least one additional slotted opening.

29. A radiator screen for generating an X-ray fan beam, comprising the slotted plate of claim 28.

30. The radiator screen of claim 29, wherein the slotted plate is movable such that the at least one additional slotted opening is positionable in a beam path of an X-ray radiation source prespecified by the radiator screen for generating the X-ray fan beam.

31. An X-ray radiator for generating an X-ray fan beam comprising:
an X-ray radiation source; and
the radiator screen of claim 29, arranged downstream of the X-ray radiation source, wherein the at least one first slotted opening includes two assigned different X-ray filter regions for X-ray spectrum differentiation is positionable in a beam path of the X-ray radiation source such that radiation components of the X-ray fan beam with different X-ray spectra are simultaneously generatable.

32. A slotted plate for limiting and shaping an X-ray fan beam, comprising:
at least one first slotted opening; and
two different X-ray filter regions for X-ray spectrum differentiation of an incident X-ray beam, the two different X-ray filter regions being permanently arranged in a region of the at least one first slotted opening such that radiation components of the incident X-ray beam penetrating the at least one first slotted opening including different X-ray spectra are simultaneously generatable, wherein a first of the two different X-ray filter regions covers a first subarea of the at least one first slotted opening and a second of the of the two different X-ray filter regions covers a remaining sub-area of the at least one first slotted opening, the slotted plate, further comprising at least one further slotted opening, wherein no X-ray filter region is arranged in a region of the at least one further slotted opening.

33. The slotted plate of claim 32, wherein dimensions of the at least one further slotted opening and dimensions of the at least one first slotted opening are identical.

34. The slotted plate of claim 33, wherein the at least one first slotted opening and the at least one further slotted opening are arranged next to one another.

35. A radiator screen for generating an X-ray fan beam, comprising the slotted plate of claim 32.

36. The radiator screen of claim 35, wherein the slotted plate is movable such that the at least one further slotted opening is positionable in a beam path of an X-ray radiation source prespecified by the radiator screen for generating the X-ray fan beam.

37. An X-ray radiator for generating an X-ray fan beam comprising:
  an X-ray radiation source; and
  the radiator screen of claim 35, arranged downstream of the X-ray radiation source, wherein the at least one first slotted opening includes two assigned different X-ray filter regions for X-ray spectrum differentiation is positionable in a beam path of the X-ray radiation source such that radiation components of the X-ray fan beam with different X-ray spectra are simultaneously generatable.

* * * * *